United States Patent [19]

Macke et al.

[11] Patent Number: 5,256,802
[45] Date of Patent: Oct. 26, 1993

[54] PROCESS FOR THE PRODUCTION OF OXIRANES

[75] Inventors: Jeffrey D. Macke, Kansas City, Mo.; Peter E. Newallis; Karl G. Steinbeck, both of LeaWood, Kans.

[73] Assignee: Miles Inc., Pittsburgh, Pa.

[21] Appl. No.: 504,784

[22] Filed: Apr. 3, 1990

[51] Int. Cl.$^5$ ............................................. C07D 301/14
[52] U.S. Cl. ................................................... 549/519
[58] Field of Search ........................................ 549/519

[56] References Cited

U.S. PATENT DOCUMENTS 3,998,856 12/1976 Rosenberger ..................... 549/519

OTHER PUBLICATIONS

Shiraki et al, Anion-catalyzed Phase-transfer Catalysis II, Bull. Chem. Soc. Japan, vol. 58, pp. 3041-3042, 1985.
Merz et al, Phase-transfer-catalyzed Production of Sulfur Ylides in an Aqueous System, Angew. Chem. Int. Ed., vol. 12, pp. 845-846, 1973.
Melvin Hatch, The Synthesis of Oxiranes from Aqueous Solutions of Simple Alkyl, Allyl, and Benzylsulfonium Salts, Jour. Org. Chem. vol. 34, pp. 2133-3137, 1968.
Bouda et al, Aldehydes and Ketones Epoxidation With Trimethylsulfonium Bromide In a Slightly Hydrated Solid-Liquid Medium, Synthetic Communications vol. 7(5), pp. 503-513 (1987).

*Primary Examiner*—C. Warren Ivy
*Assistant Examiner*—Ba K. Trinh
*Attorney, Agent, or Firm*—Joseph C. Gil; Lyndanne M. Whalen

[57] ABSTRACT

Oxiranes are made from ketones by heating a ketone which is preferably an alkyl ketone to a temperature of from about 60° to about 90° C. (preferably about 80° C.) in the presence of a sulfonium salt, a quaternary ammonium salt and a potassium hydroxide solution which is at least 61% potassium hydroxide. It is preferred that no organic solvent be included in the reaction mixture. The potassium hydroxide is generally included in an amount such that for every mole of ketone, from about 3 to about 4 moles of potassium hydroxide are present. The sulfonium salt is generally used in an amount of at least 1.1 moles for each mole of ketone. The quaternary ammonium salt is generally used in an amount of from about 1 to about 5 mol % based on moles of ketone present.

12 Claims, No Drawings

PROCESS FOR THE PRODUCTION OF OXIRANES

BACKGROUND OF THE INVENTION

The present invention relates to a process for the production of oxiranes from ketones.

Processes for the production of oxiranes from ketones under aqueous conditions are known. For example, Shiraki, et al, "Anion-catalyzed Phase-transfer Catalysis. II. Effects of Anionic Tetrakis[3,5-bis(trifluoromethyl)phenyl]borate Catalyst in Phase-transfer-catalyzed Sulfonium Ylide Formation", *Bull. Chem. Soc. Japan*, Vol.58, pages 3041–3042 (1985) discloses use of tetrakis[3,5-bis(trifluoromethyl)phenyl]borate anion to promote formation of oxiranes from carbonyl substrates and trimethylsulfonium chloride in a two-phase mixture of dichloromethane and up to 50 wt % aqueous solutions of sodium hydroxide.

Merz et al, "Phase-transfer-catalyzed Production of Sulfur Ylides in an Aqueous System", *Angew.Chem.Internat.Edit.*, Vol. 12, pages 845–846 (1973) discloses the use of tetrabutylamonium iodide in a two-phase system of dichloromethane and aqueous sodium hydroxide to produce oxiranes from aldehydes. This report also teaches that good yields of oxirane are not obtained when ketones rather than aldehydes are used as the starting material.

Hatch, "The Synthesis of Oxiranes from Aqueous Solutions of Simple Alkyl, Allyl, and Benzylsulfonium Salts", *Journal of Organic Chemistry*, Vol. 34, pages 2133–2137 (July 1969) describes the results obtained when simple sulfonium salts react with warm aqueous sodium hydroxide and carbonyl compounds to produce oxiranes. The results indicate that the oxirane yield obtained from various aldehydes is substantially dependent upon the specific type of sulfonium salt used. The results also led Hatch to conclude that reactions of the type disclosed therein are subject to structural factors (i.e., structural differences in reactants are significant), reaction conditions, and the possibility for side reactions.

SUMMARY OF THE INVENTION

It is an object of the present invention to provide a process for the production of oxiranes from ketones in high yields in an aqueous system.

It is also an object of the present invention to provide a process for the production of oxiranes in high yield in relatively short reaction times.

It is a further object of the present invention to provide a more economical process for the production of oxiranes from ketones.

These and other objects which will be apparent to those skilled in the art are accomplished by heating a ketone in the presence of a sulfonium salt, a quaternary ammonium salt and an aqueous potassium hydroxide solution in which potassium hydroxide is present in at least 61 wt % to a temperature of from about 60° to about 90° C. In a preferred embodiment, 3–4 moles of potassium hydroxide, 1–5 mol % quaternary ammonium salt and at least 1.1 moles of sulfonium salt are present for each mole of ketone present.

DETAILED DESCRIPTION OF THE PREFERRED EMBODIMENTS OF THE INVENTION

The present invention is a process for the production of oxiranes from ketones. In this process, a ketone is heated to a temperature of from about 60° to about 90° C. in the presence of an aqueous potassium hydroxide solution, a sulfonium salt and a quaternary ammonium salt. A key feature of the present invention is the use of a concentrated potassium hydroxide solution. The solutions suitable for use in the present invention must contain at least 61 wt % of potassium hydroxide if the oxiranes are to be obtained in high yield in relatively short reaction times.

Ketones suitable for use in the process of the present invention include most alkyl- and aryl aldehydes and ketones, 1-(4-chlorophenyl)-4,4-dimethyl-3-pentanone, being particularly preferred.

In theory it would be possible to use any of the known sulfonium salts in the process of the present invention. The sulfonium salts which have been found to be particularly useful in the process of the present invention are trimethylsulfonium bromide and trimethylsulfonium chloride with the bromide being particularly preferred. This sulfonium salt generally should be used in an amount such that for every mole of ketone present in the reaction mixture, at least 1.1–1.3 and preferably at least 1.5 moles of sulfonium salt are present.

Any quaternary ammonium salt could be used in the practice of the present invention. Examples of suitable ammonium salts include: tetrabutylammonium bromide, tetrahexylammonium bromide with myristyltrimethylammonium bromide being particularly preferred. The quaternary ammonium salt is generally used in a quantity such that for every mole of ketone present in the reaction mixture, 1–5 mol % and preferably about 2 mol % of ammonium salt is present.

The aqueous potassium hydroxide solutions used in the process of the present invention should contain at least 61 wt % potassium hydroxide and are generally used in an amount such that for every mole of ketone present in the reaction mixture, from about 3.0 to about 4.0 moles, preferably about 4.0 moles of potassium hydroxide are present. Increasing the potassium hydroxide concentration does improve the conversion rate.

It is preferred that the process of the present invention be carried out in the absence of organic solvents. It is possible, however, to include such solvents but use of such solvents may result in reduced oxirane yields. If used, suitable solvents include toluene, dichlorobenzene, and xylene.

The reaction temperature is generally in the range from about 60° to about 90° C. with a temperature of about 80° C. being particularly preferred. The optimum reaction temperature will of course be dependent upon the specific materials being used and the reaction time desired.

The reaction times for the process of the present invention generally range from about 2 to about 8 hrs depending on the substrate and reaction conditions.

Any of the known reactors capable of withstanding the reaction environment of the process of the present invention may be used.

The oxiranes produced in accordance with the present invention can be obtained in yields of about 70–95%. These compounds are useful as intermediates in the production of a wide variety of materials including fungicides.

Having thus described our invention, the following examples are given as being illustrative thereof. All parts and percentages are parts by weight and percentages by weight, unless otherwise indicated.

EXAMPLES

EXAMPLE 1

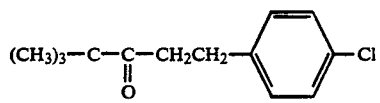   I

Alkylketone I (22.9 gm, 0.10 mol), trimethylsulfonium bromide (23.6 gm, 0.15 mol), aqueous potassium hydroxide (27.8 gm, 0.42 mol, 62% solution) and myristyltrimethylammonium bromide (1.0 gm, 2.97 mmol) were charged to a reaction vessel and heated to 80° C. The mixture was heated at 80° C. for 6 hrs using gas chromatography to monitor the progress of the reaction. The results of this analysis are given in the table below.

After the mixture was allowed to cool, water (200 ml) and toluene (100 ml) were added, the mixture was agitated, and the phases were allowed to separate. The aqueous phase was extracted with toluene (twice with 200 ml each time), the toluene phases were combined, and the solvent removed under reduced pressure to give the oxirane in 69% net yield.

| Cook Time (hr) | Cook Temp. (°C.) | GC Area % Alkylketone | GC Area % Epoxide |
|---|---|---|---|
| 1 | 78 | 26.8 | 72.7 |
| 2 | 79 | 17.4 | 82.6 |
| 3 | 79 | 11.6 | 86.7 |
| 4 | 79 | 8.8 | 89.1 |
| 5 | 79 | 7.6 | 90.6 |
| 6 | 80 | 6.2 | 89.8 |
| overnight | room | 6.5 | 91.8 |

EXAMPLE 2

A 61% aqueous KOH solution (1101.6 gm, 12.1 mol) at 80° C. was added dropwise (15 min) to a stirred mixture of alkylketone I (688.0 gm, 3.00 mol), and myristyltrimethylammonium bromide (30.0 gm, 0.089 mol) at 80° C. The mixture was heated at 80° C. and the progress of the reaction was monitored by gas chromatography. The results were as follows:

| Cook Time (hr) | Cook Temp. (°C.) | GC Area % Alkylketone | GC Area % Epoxide |
|---|---|---|---|
| 1 | 80 | 27.44 | 72.6 |
| 2 | 80 | 7.37 | 92.6 |
| 3 | 80 | 2.38 | 97.6 |

Toluene (500 gm) and water (800 gm) were added and the mixture was agitated for 30 minutes. The phases were separated and the oxirane was recovered in 90% yield.

EXAMPLES 3-23

The alkylketone corresponding to the formula given in Example 1, trimethylsulfonium bromide, potassium hydroxide, a specified phase-transfer catalyst and optionally a specified solvent were heated under the conditions specified in Table 1 below. The results of each of these experiments are reported in Table 1.

EXAMPLE 24

The alkylketone corresponding to the formula given in Example 1, trimethylsulfonium bromide, sodium hydroxide, and a specified phase-transfer catalyst were heated under the conditions specified in Table 1 below. The result of this experiment is also reported in Table 1.

EXAMPLES 25-26

The alkylketone corresponding to the formula given in Example 1, trimethylsulfonium chloride, potassium hydroxide, and a specified phase-transfer catalyst were heated under the conditions specified in Table 1 below. The results of each of these experiments are reported in Table 1.

TABLE 1

| | | | | | | | | | |
|---|---|---|---|---|---|---|---|---|---|
| Conversion of Alkylketone to Epoxide Using Aqueous Base | | | | | | | | | |
| Example | Solvent | Phase Transfer Catalyst | KOH Add °C. | Cook °C. | Cook Time hrs | Add Rate of KOH | grams Sol'n KOH (%) | % Epoxide[1] | Alkyl-Ketone |
| 3 | Toluene | MTMAB | 20 | 90R* | 5.0 | 15 min | 99.8 (17.3) 0.31 mol | 0.6 | 0.10M |
| 4 | Toluene | Dowex-1 resin | 21 | 88-82R* | 6.0 | 15 min | 36.8 (46.9) 0.31 mol | 2.2 | 0.10M |
| 5 | Toluene | Aliquot | 20 | 89-84R* | 6.0 | 15 min | 36.8 (46.9) 0.31 mol | 9.0 | 0.10M |
| 6 | Toluene | Polyvinyl pyridine | 20 | 97-82R* | 6.0 | 15 min | 36.8 (46.9) 0.31 mol | 0 | 0.10M |
| 7 | Toluene | THAB | 25 | 89-77R* | 5.0 | 15 min | 33.8 (51.1) 0.31 mol | 15.5 | 0.10M |
| 8 | — | MTMAB | 20 | 80 | 5.5 | 15 min | 33.8 (51.1) 0.31 mol | 34.7 | 0.10M |
| 9 | — | MTMAB | 60 | 60 | 9.5 | 2.0 hrs | 33.8 (51.1) 0.31 mol | 37.9 | 0.10M |
| 10 | — | MTMAB | 21 | 80 | 6.0 | 15 min | 27.8 (62.1) 0.31 mol | 91.8 | 0.10M |
| 11 | — | MTMAB | 80 | 80 | 6.0 | 2.0 hrs | 27.8 (62.1) 0.31 mol | 87.7 | 0.10M |
| 12 | — | MTMAB | 76-94 | 90 | 4.0 | 2.0 hrs | 27.8 (62.1) 0.31 mol | 84.9 | 0.10M |
| 13 | Toluene 23.6 g | MTMAB 2.0 g | 72-86 | 83-87 | 2.0 | 2.3 hrs | 27.8 (62.1) 0.31 mol | 81.4 | 0.10M |
| 14 | — | MTMAB | 21 | 70 | 5.0 | 15 min | 27.8 (62.1) | 81.1 | 0.10M |

TABLE 1-continued

Conversion of Alkylketone to Epoxide Using Aqueous Base

| Example | Solvent | Phase Transfer Catalyst | KOH Add °C. | Cook °C. | Cook Time hrs | Add Rate of KOH | grams Sol'n KOH (%) | % Epoxide[1] | Alkyl-Ketone |
|---|---|---|---|---|---|---|---|---|---|
| | | | | | 12.0 | | 0.31 mol | 89.4 | |
| 15 | — | DEB/MTMAB | 21 | 80 | 5.0 | 15 min | 27.8 (62.1) 0.31 mol | 86.0 | 0.10M |
| 16 | — | — | 21 | 80 | 6.5 | 15 min | 27.8 (62.1) 0.31 mol | 49.3 | 0.10M |
| 17 | — | DEG | 21 | 80 | 4.0 | 15 min | 27.8 (62.1) 0.31 mol | 73.4 | 0.10M |
| 18 | — | MTMAB | 21 | 80 | 6.0 | 15 min | 27.8 (62.1) 0.31 mol | ca.86 | 0.10M |
| Charged initial 0.1M Epoxide | | | | | | | | | |
| 19 | — | MTMAB | 23 | 80 | 5.0 | 15 min | 23.2 (62.1) 0.25 mol | 71.5 | 0.10M |
| 20 | — | MTMAB | 23 | 80 | 4.0 | 15 min | 18.5 (62.1) 0.20 mol | 82.9 | 0.10M |
| 21 | — | MTMAB | 80 | 80 | 4.5 | 2.0 hrs | 27.8 (62.1) 0.31 mol | 89.2 | 0.10M |
| Salt added over 2.0 hrs | | | | | | | | | |
| 22 | — | MTMAB | 21 | 80 | 7.0 | 15 min | 32.4 (61.4) 0.35 mol | 93.1 | 0.10M |
| 23 | — | MTMAB | 21 | 80 | 6.0 | 15 min | 37.1 (61.3) 0.4 mol | 96.7 | 0.10M |
| 24 | — | MTMAB | 21 | 80 | 7.5 | 15 min | 50% NaOH 0.4 mol | 36.4 | 0.10M |
| 25 | — | MTMAB | 21 | 80 | 1.0 | 15 min | 37.1 (61.3) 0.4 mol | 86.2 | 0.10M |
| 26 | — | MTMAB | 21 | 70 | 3.0 | 15 min | 37.1 (61.3) 0.4 mol | 94.7 | 0.10M |

R* = Reflux
MTMAB - Myristyltrimethylammonium Bromide
THAB - Tetrahexylammonium Bromide
[1]GC Area %

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an oxirane from a ketone comprising heating (a) a ketone in the presence of (b) an aqueous potassium hydroxide solution in which at least 61% by weight of the solution is potassium hydroxide, (c) a sulfonium salt and (d) a quaternary ammonium salt to a temperature of from about 60° to about 90° C.

2. The process of claim 1 in which the sulfonium salt (c) is trimethylsulfonium bromide.

3. The process of claim 2 in which the quaternary ammonium salt (d) is myristyltrimethyl ammonium bromide.

4. The process of claim 3 in which 3.0–4.0 moles of potassium hydroxide are present for each mole of ketone (a).

5. The process of claim 4 in which the quaternary ammonium salt (d) is present in an amount of from about 1 to about 5 mol % based on moles of ketone (a).

6. The process of claim 5 in which the sulfonium salt (c) is present in an amount of at least 1.1 moles for each mole of ketone (a).

7. The process of claim 1 in which the sulfonium salt (c) is trimethylsulfonium chloride.

8. The process of claim 1 in which the quaternary ammonium salt (d) is myristyltrimethyl ammonium bromide.

9. The process of claim 1 in which 3.0–4.0 moles of potassium hydroxide are present for each mole of ketone (a).

10. The process of claim 1 in which quaternary ammonium salt (d) is present in an amount of from about 1 to about 5 mol % based on moles of ketone (a).

11. The process of claim 1 in which the sulfonium salt (c) is present in an amount of at least 1.1 moles for each mole of ketone (a).

12. The process of claim 1 in which the mixture of (a), (b), (c) and (d) is heated to a temperature of about 80° C.

* * * * *